United States Patent
Toepke et al.

(10) Patent No.: US 9,709,973 B2
(45) Date of Patent: Jul. 18, 2017

(54) HANDHELD FIELD MAINTENANCE TOOL WITH IMPROVED DIAGNOSTICS

(75) Inventors: Todd M. Toepke, Eden Prairie, MN (US); Christopher P. Kantzes, Minneapolis, MN (US); Brad N. Mathiowetz, Lakeville, MN (US); Kun Yang, Eden Prairie, MN (US); Adam E. Lund, St. Louis Park, MN (US)

(73) Assignee: Fisher-Rosemount Systems, Inc., Austin, TX (US)

( * ) Notice: Subject to any disclaimer, the term of this patent is extended or adjusted under 35 U.S.C. 154(b) by 206 days.

(21) Appl. No.: 13/191,644

(22) Filed: Jul. 27, 2011

(65) Prior Publication Data
US 2012/0038458 A1    Feb. 16, 2012

Related U.S. Application Data

(60) Provisional application No. 61/368,477, filed on Jul. 28, 2010.

(51) Int. Cl.
   G08B 5/22        (2006.01)
   G08B 25/00       (2006.01)
   (Continued)

(52) U.S. Cl.
   CPC ....... G05B 19/042 (2013.01); G05B 19/0426 (2013.01); *G05B 2219/23018* (2013.01);
   (Continued)

(58) Field of Classification Search
   CPC .............. G05B 19/042; G05B 19/0428; G05B 2219/24048; G05B 2219/24067;
   (Continued)

(56) References Cited

U.S. PATENT DOCUMENTS

| 5,195,392 A | 3/1993 | Moore et al. ................. 73/866.5 |
| 5,309,351 A | 5/1994 | McCain et al. ............... 364/132 |

(Continued)

FOREIGN PATENT DOCUMENTS

| CN | 101763576 | 6/2010 |
| DE | 10245176  | 4/2004 |

(Continued)

OTHER PUBLICATIONS

Industrial Scientific, The Gas Detection People; Accessed Sep. 4, 2013; Copyright 1988, 1996, p. 5.*

(Continued)

*Primary Examiner* — Emily C Terrell
(74) *Attorney, Agent, or Firm* — Christopher R. Christenson; Kelly, Holt & Christenson PLLC

(57) ABSTRACT

A handheld field maintenance tool with improved diagnostic functions is provided. The tool includes a process communication module configured to interact with a field device. A controller is coupled to the process communication module. The controller is configured to execute a number of improved diagnostic functions relative to the field device. The controller may obtain contextual information relative to a current field maintenance operation and preload at least one resource relative to a next field operation step. The controller may obtain process alarm information through a wireless communication module, and field device alert information through the process communication module and provide an indication on a display relative to both process alarm information and field device alert information. The controller may execute a sequence of field device maintenance operations on the field device in response to a signal from a user input device. The controller may obtain snapshot information in response to a signal from a user input device.

24 Claims, 8 Drawing Sheets

(51) Int. Cl.
*G05B 11/01* (2006.01)
*G08C 19/16* (2006.01)
*G05B 19/042* (2006.01)

(52) U.S. Cl.
CPC .......... *G05B 2219/23054* (2013.01); *G05B 2219/23126* (2013.01); *G05B 2219/23163* (2013.01); *G05B 2219/23406* (2013.01); *G05B 2219/23445* (2013.01); *G05B 2219/23446* (2013.01); *G05B 2219/24001* (2013.01); *G05B 2219/24056* (2013.01); *G05B 2219/25062* (2013.01); *G05B 2219/25428* (2013.01); *G05B 2219/31121* (2013.01); *G05B 2219/31197* (2013.01); *G05B 2219/31475* (2013.01); *G05B 2219/32007* (2013.01); *G05B 2219/32144* (2013.01); *G05B 2219/32226* (2013.01); *G05B 2219/33331* (2013.01); *G05B 2219/35422* (2013.01); *G05B 2219/35429* (2013.01); *G05B 2219/36122* (2013.01); *G05B 2219/36128* (2013.01); *Y02P 90/14* (2015.11)

(58) Field of Classification Search
CPC .......... G05B 23/0283; G06F 11/3058; G01N 35/00594; F17D 5/02; G01F 25/00; G01F 25/0007; G01M 3/2807; G01M 3/2815; G01M 3/3263
See application file for complete search history.

(56) References Cited

U.S. PATENT DOCUMENTS

| | | | |
|---|---|---|---|
| 5,442,632 A | 8/1995 | Crowder et al. | 371/20.1 |
| 5,650,940 A * | 7/1997 | Tonozuka et al. | 709/224 |
| 5,903,455 A | 5/1999 | Sharpe, Jr. et al. | 364/188 |
| 6,033,226 A | 3/2000 | Bullen | 434/219 |
| 6,211,649 B1 | 4/2001 | Matsuda | 320/115 |
| 6,236,223 B1 | 5/2001 | Brady et al. | 324/750.3 |
| 6,377,859 B1 | 4/2002 | Brown et al. | 700/79 |
| 6,591,201 B1 * | 7/2003 | Hyde | 702/45 |
| 6,633,782 B1 | 10/2003 | Schleiss et al. | 700/26 |
| 6,697,894 B1 * | 2/2004 | Mitchell | G06F 1/163 |
| | | | 361/679.4 |
| 6,714,846 B2 * | 3/2004 | Trsar | G07C 5/0808 |
| | | | 701/29.1 |
| 6,725,182 B2 | 4/2004 | Pagnano et al. | 702/188 |
| 6,961,586 B2 * | 11/2005 | Barbosa | G06Q 10/06 |
| | | | 455/556.1 |
| 6,971,063 B1 | 11/2005 | Rappaport et al. | 715/733 |
| 6,975,219 B2 | 12/2005 | Eryurek et al. | |
| 7,013,184 B2 | 3/2006 | Romagnoli et al. | 700/17 |
| 7,120,391 B2 | 10/2006 | Stengele et al. | 455/41.3 |
| 7,188,200 B2 | 3/2007 | Griech | 710/100 |
| 7,245,271 B2 | 7/2007 | Nixon et al. | |
| 7,251,534 B2 * | 7/2007 | Walls et al. | 700/17 |
| 7,308,331 B2 * | 12/2007 | Bjornson | G05B 23/0278 |
| | | | 340/3.43 |
| 7,337,369 B2 | 2/2008 | Barthel et al. | 714/43 |
| 7,400,255 B2 | 7/2008 | Horch | 340/572.7 |
| 7,402,086 B2 * | 7/2008 | Pomerantz | H01R 13/64 |
| | | | 439/680 |
| 7,454,252 B2 | 11/2008 | El-Sayed | 700/21 |
| 7,505,819 B2 | 3/2009 | El-Sayed | 700/21 |
| 7,506,812 B2 | 3/2009 | von Mueller et al. | 235/449 |
| 7,675,406 B2 | 3/2010 | Baier et al. | 340/506 |
| 7,733,833 B2 | 6/2010 | Kalika et al. | 370/338 |
| 7,797,061 B2 | 9/2010 | El-Sayed | 700/21 |
| 8,000,815 B2 | 8/2011 | John et al. | 700/18 |
| 8,036,007 B2 | 10/2011 | Woehrle | 363/65 |
| 8,059,101 B2 | 11/2011 | Westerman et al. | 345/173 |
| 8,060,862 B2 | 11/2011 | Eldridge et al. | 717/121 |
| 8,060,872 B2 | 11/2011 | Da Silva Neto | 717/177 |
| 8,074,172 B2 | 12/2011 | Kocienda et al. | 715/263 |
| 8,086,175 B2 * | 12/2011 | Nakagawa | G05B 19/042 |
| | | | 342/357.2 |
| 8,112,669 B2 * | 2/2012 | Zimmerman | G06F 11/2294 |
| | | | 714/27 |
| 8,126,145 B1 | 2/2012 | Tewari et al. | 380/255 |
| 8,150,462 B2 | 4/2012 | Guenter et al. | 455/557 |
| 8,180,948 B2 | 5/2012 | Kreider et al. | 710/313 |
| 8,214,243 B2 * | 7/2012 | Graham et al. | 705/7.22 |
| 8,224,256 B2 | 7/2012 | Citrano, III et al. | 455/67.11 |
| 8,782,539 B2 * | 7/2014 | Bump et al. | 715/762 |
| 2001/0047504 A1 | 11/2001 | Aoyama | 714/799 |
| 2002/0004370 A1 | 1/2002 | Stengele et al. | 455/39 |
| 2002/0007237 A1 | 1/2002 | Phung et al. | 701/33 |
| 2002/0027504 A1 | 3/2002 | Davis et al. | 340/540 |
| 2002/0086642 A1 | 7/2002 | Ou et al. | 455/69 |
| 2002/0167904 A1 | 11/2002 | Borgeson et al. | 702/183 |
| 2002/0171558 A1 | 11/2002 | Bartelheim et al. | 340/825.49 |
| 2003/0050737 A1 | 3/2003 | Osann, Jr. | 700/276 |
| 2003/0109937 A1 | 6/2003 | Zielinski et al. | 700/1 |
| 2003/0200058 A1 * | 10/2003 | Ogawa et al. | 702/184 |
| 2003/0204373 A1 | 10/2003 | Zielinski et al. | 702/184 |
| 2003/0229472 A1 | 12/2003 | Kantzes et al. | 702/183 |
| 2004/0039458 A1 | 2/2004 | Mathiowetz et al. | 700/17 |
| 2004/0111238 A1 | 6/2004 | Kantzes et al. | 702/183 |
| 2004/0193287 A1 | 9/2004 | Lefebvre et al. | 700/1 |
| 2004/0204193 A1 | 10/2004 | Li et al. | 455/575.1 |
| 2004/0228184 A1 | 11/2004 | Mathiowetz | 365/202 |
| 2004/0230327 A1 | 11/2004 | Opheim et al. | 700/83 |
| 2004/0234338 A1 * | 11/2004 | Monroe et al. | 405/54 |
| 2005/0010323 A1 * | 1/2005 | Cocciadiferro et al. | 700/174 |
| 2005/0114086 A1 | 5/2005 | Zielinski et al. | 702/183 |
| 2005/0164684 A1 | 7/2005 | Chen et al. | 455/414.1 |
| 2005/0180437 A1 * | 8/2005 | Twomey | H04L 12/42 |
| | | | 370/401 |
| 2005/0210278 A1 * | 9/2005 | Conklin | G06F 21/80 |
| | | | 713/194 |
| 2005/0222698 A1 | 10/2005 | Eryurek et al. | 700/90 |
| 2005/0223120 A1 | 10/2005 | Scharold et al. | 710/1 |
| 2006/0014533 A1 | 1/2006 | Warren | 455/423 |
| 2006/0073464 A1 * | 4/2006 | Baldus et al. | 434/350 |
| 2006/0085108 A1 * | 4/2006 | Grier | G05B 23/0248 |
| | | | 701/29.1 |
| 2006/0087402 A1 | 4/2006 | Manning et al. | 340/3.1 |
| 2006/0095230 A1 * | 5/2006 | Grier | G05B 23/0216 |
| | | | 702/183 |
| 2006/0155908 A1 | 7/2006 | Rotvold et al. | 710/315 |
| 2006/0206277 A1 | 9/2006 | Horch | 702/82 |
| 2006/0290496 A1 | 12/2006 | Peeters | 340/572.1 |
| 2006/0291438 A1 | 12/2006 | Karschnia et al. | 370/338 |
| 2007/0161352 A1 | 7/2007 | Dobrowski et al. | 455/69 |
| 2007/0161371 A1 | 7/2007 | Dobrowski et al. | 455/423 |
| 2007/0179645 A1 | 8/2007 | Nixon et al. | 700/83 |
| 2007/0208279 A1 | 9/2007 | Panella et al. | 600/595 |
| 2008/0114911 A1 | 5/2008 | Schumacher | 710/72 |
| 2008/0234837 A1 | 9/2008 | Samudrala et al. | 700/19 |
| 2008/0268784 A1 | 10/2008 | Kantzes et al. | 455/66.1 |
| 2008/0275605 A1 * | 11/2008 | Murphy et al. | 701/33 |
| 2009/0065578 A1 | 3/2009 | Peterson et al. | 235/382 |
| 2009/0094466 A1 | 4/2009 | Matthew et al. | 713/300 |
| 2009/0125713 A1 | 5/2009 | Karschnia et al. | 713/153 |
| 2009/0171483 A1 | 7/2009 | Scheuermann | 700/83 |
| 2009/0177970 A1 | 7/2009 | Jahl et al. | 717/735 |
| 2009/0248362 A1 * | 10/2009 | Manegold et al. | 702/183 |
| 2009/0271726 A1 | 10/2009 | Gavimath et al. | 715/771 |
| 2009/0284390 A1 | 11/2009 | Lahner et al. | 340/825.49 |
| 2009/0296601 A1 | 12/2009 | Citrano et al. | 370/254 |
| 2009/0326852 A1 | 12/2009 | Vetter et al. | 702/108 |
| 2010/0061703 A1 * | 3/2010 | Pham | G08B 21/02 |
| | | | 386/241 |
| 2010/0100766 A1 | 4/2010 | Bengtsson et al. | 714/23 |
| 2010/0114347 A1 | 5/2010 | Dheenathayalan et al. | 700/97 |
| 2010/0114549 A1 | 5/2010 | Kolavi | 703/13 |
| 2010/0145476 A1 | 6/2010 | Junk et al. | 700/7 |
| 2010/0220630 A1 | 9/2010 | Kalika et al. | 370/254 |
| 2010/0290084 A1 | 11/2010 | Russell, III et al. | 358/1.15 |
| 2010/0290351 A1 | 11/2010 | Toepke et al. | 370/250 |
| 2010/0290359 A1 | 11/2010 | Dewey et al. | 370/252 |
| 2010/0293363 A1 | 11/2010 | Meyer et al. | 713/1 |
| 2011/0117529 A1 | 5/2011 | Barash et al. | 434/265 |

(56) References Cited

U.S. PATENT DOCUMENTS

| | | | |
|---|---|---|---|
| 2011/0238188 A1 | 9/2011 | Washiro | 700/19 |
| 2012/0038548 A1 | 2/2012 | Toepke et al. | 345/156 |
| 2012/0038760 A1 | 2/2012 | Kantzes et al. | 348/61 |
| 2012/0040316 A1 | 2/2012 | Mathiowetz et al. | 434/219 |
| 2012/0040698 A1 | 2/2012 | Ferguson et al. | 455/457 |
| 2012/0041744 A1 | 2/2012 | Kantzes et al. | 703/13 |
| 2012/0046911 A1 | 2/2012 | Mathiowetz et al. | 702/184 |
| 2013/0103353 A1* | 4/2013 | Kloppner | 702/182 |

FOREIGN PATENT DOCUMENTS

| | | |
|---|---|---|
| DE | 102007035158 | 1/2009 |
| DE | 102008029406 | 12/2009 |
| DE | 102009028195 | 2/2011 |
| EP | 1515208 | 3/2005 |
| EP | 1916582 | 4/2008 |
| EP | 2071427 | 6/2009 |
| EP | 2077473 | 7/2009 |
| EP | 2148259 | 1/2010 |
| EP | 2204705 | 7/2010 |
| GB | 2382418 | 5/2003 |
| GB | 2 394 124 | 4/2004 |
| JP | 9051583 | 2/1997 |
| JP | 2001337004 | 7/2001 |
| JP | 2007080194 A | 3/2007 |
| JP | 2007-91381 | 4/2007 |
| JP | 2008165193 | 7/2008 |
| JP | 2009086983 A | 4/2009 |
| KR | 20060078883 | 7/2006 |
| WO | WO 01/35190 | 5/2001 |
| WO | WO 02/086662 | 10/2002 |
| WO | WO 2006/016845 | 2/2006 |
| WO | W02006053211 A2 | 5/2006 |
| WO | WO 2008/042074 | 4/2008 |
| WO | WO 2008/077358 | 7/2008 |
| WO | WO 2008/096216 | 8/2008 |
| WO | WO 2008/127632 | 10/2008 |
| WO | WO 2009/003146 | 12/2008 |
| WO | WO 2009/003148 | 12/2008 |
| WO | WO 2009/074544 | 6/2009 |

OTHER PUBLICATIONS

Merriam Webster "Context" definition, accessed Jan. 30, 2013, screen capture Jan. 18, 2006.*
Merriam Webster "Snapshot" definition, accessed Jan. 30, 2013, screen capture Apr. 22, 2009.*
Invitation to Pay Additional Fees for international patent application No. PCT/US2010/034889 dated Sep. 15, 2010.
ABB Limited: "Wireless Instrumentation Jargon Buster". Information bulletin instrumentation ABB No. IB/INST-018, Mar. 3, 2009, XP002596601. Retrieved from the Internet: URL:http://www05.abb.com/global/scot/scot203.nsf/veritydisplay/be00ec76ef07e978c125756e003157b9/$File/IB_INST_018_1.pdf.
Notification of Transmittal of the International Search Report and the Written Opinion from the International Application No. PCT/US2010/021764.
David Gustafsson: "WirelessHART—Implementation and Evaluation on Wireless Sensors". Masters's Degree Project, KTH University, Electrical Engineering, Apr. 1, 2009, pp. 1-39, XP002596602, Stockholm, Sweden. Retrieved from the Internet: URL:http://www.ee.kth.se/php/modules/publications/reports/2009/XR-EE-RT%202009:003.pdf.
Notification of Transmittal of the International Search Report and the Written Opinion for the International application No. PCT/US2010/034848 dated Aug. 26, 2010.
Possio Bluetooth to WLAN Gateway PX20: Full Product Description retrieved from http://www.blueunplugged.com/p.aspx?p=105816.
1420 Wireless Gateway: Product Data Sheet 00813-0100-4420, Rev BA Mar. 2008. Emerson Process Management.
Smart Wireless Gateway (WirelessHART™). Quick installation Guide 00825-0200-4420, Rev BA. Aug. 2009. Emerson Process Management.
Rosemount 3051S Wireless Series Scalable Pressure, Flow, and Level Solutions. Reference Manual 00809-0100-4802, rev BA. Aug. 2007. Emerson Process Management.
EPO Communication pursuant to Rules 161(1) and 162 EPC for European patent application No. 10701430.0 dated Aug. 30, 2011.
Invitation to Pay Additional Fees for international patent application No. PCT/US2010/034949 dated Sep. 17, 2010.
Technical Data Sheet: VIATOR® USB HART® Interface (Model 010031). MACTek Measurement and Control Technologies.
VIATOR® Bluetooth® Wireless Technology Interface for use with HART field devices. MACTek Measurement and Control Technologies retrieved from www.mactekcorp.com/product5.htm.
Product Data Sheet: VIATOR RS232. MACTek Measurement and Control Technologies retrieved from www.mactekcorp.com/product1.htm.
Notification of Transmittal of the International Search Report and the Written Opinion from the International Application No. PCT/US2010/034889.
Notification of Transmittal of the International Search Report and the Written Opinion from the International Application No. PCT/US2010/034949.
EPO Communication from related European application No. 10730279.6 dated Jan. 13, 2012.
EPO Communication from related European application No. 10730281.2 dated Jan. 13, 2012.
EPO Communication from related European application No. 10725543.2 dated Jan. 12, 2012.
Rosemount 3051SMV Quick Installation Guide 00825-0100-4803 Rev BA. Apr. 2011.
Invitation to Pay Additional Fees from the International Application No. PCT/US2011/045673 dated Jan. 16, 2012.
Notification of Transmittal of the International Search Report and the Written Opinion from the International Application No. PCT/US2011/045680 dated Jul. 6, 2012.
Notification of Transmittal of the International Search Report and the Written Opinion from the International Application No. PCT/US2011/045681 dated Jan. 5, 2012.
475 Field Communicator. User's Guide XP007919976. Aug. 2009. www.fieldcommunicator.com by Emerson Process Management.
1420 Wireless Gateway. Reference Manual 00809-0100-4420. Rev BA. Aug. 2007. Emerson Process Management.
Invitation to pay additional fees from the related international patent application No. PCT/US2011/045679 dated Aug. 6, 2012.
Invitation to pay additional fees from the related International patent application No. PCT/US2011/045664 dated Aug. 9, 2012.
Invitation to pay additional fees from the related International patent application No. PCT/US2011/045676 dated Jul. 30, 2012.
First Communication from related European patent application No. 107392796 dated Oct. 19, 2012.
Office Action from related Russian application No. 2011151063 dated Nov. 12, 2012.
First Office Action from related Japanese application No. 2015511048, dated Jan. 29, 2013.
Lee S W et al: "Honam Petrochemical Corporation Uses Simulator for Ethylene Plant Operator Training", Processing of the Industrial Computing Conference. Houston, Oct. 18-23, 1992, pp. 219-222.
Kurrle H-P et al.: "Trainingssimulator Aur Ausbildung Von Chemikanten und Anlagenfahrern. Otraining Simulator For the Training of Process Workers (Chemikanten) and Operators", Automatisierungstechnische Praxis—ATP, Oldenbourg Indusrieverlag, Munchen, DE, vol. 36. No. 7. Jul. 1, 1994. Abstract. Section 2.
Invitation to pay additional fees from the related international patent application No. PCT/US2011/045665 dated Aug. 23, 2012.
Bushman J B: "Ally: An Operator's Associate for Cooperative Supervisory Control Systems", IEEE Transactions on Systems, Man and Cybernetics, IEEE Inc. New York, US. vol. 23, No. 1, Jan. 1, 1993, pp. 111-128.

(56) References Cited

OTHER PUBLICATIONS

First Communication for the related European patent application No. 107302812 dated Oct. 11, 2012.
International Search Report and Written Opinion from the related International patent application No. PCT/US2011/045664 dated Nov. 6, 2012.
International Search Report and Written Opinion from the related International patent application No. PCT/US2011/045679 dated Nov. 6, 2012.
International Search Report and Written Opinion from the related International patent application No. PCT/US2011/045665 dated Nov. 6, 2012.
First Communication from related European patent application No. 107255432 dated Oct. 11, 2012.
First Office Action from related Japanese patent application No. 2013-521964, dispatched on Jan. 21, 2014. 9 pages.
Notification on the results of patentability check from Russian counterpart application No. 2013108860, dated May 28, 2014. 9 pages.
Office Action from Canadian patent application No. 2,806,242 dated Jul. 28, 2014. 6 pages.
Office Action from Counterpart Chinese Patent Application No. 201180001614.6, issuing date: Dec. 25, 2014, 9 pages with English translation.
Decision on Refusal to Grant a Patent for Invention for Russian Application No. 2013108860, dated Mar. 30, 2015, 15 pages with English Translation.
Canadian patent application No. 2,806,242, from Oct. 7, 2015, 6 pages.
Office Action for Chinese Patent Application No. 201510374161.1, dated Apr. 24, 2017, 9 pages including English translation.

\* cited by examiner

HANDHELD FIELD MAINTENANCE TOOL WITH IMPROVED DIAGNOSTICS

CROSS-REFERENCE TO RELATED APPLICATION

The present application is based on and claims the benefit of U.S. provisional patent application Ser. No. 61/368,477, filed Jul. 28, 2010, the content of which is hereby incorporated by reference in its entirety.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998. An example of a handheld field maintenance tool that complies with intrinsic safety requirements includes that sold under trade designation Model 475 Field Communicator, available from Emerson Process Management of Austin, Tex.

SUMMARY

A handheld field maintenance tool with improved diagnostic functions is provided. The tool includes a process communication module configured to interact with a field device. A controller is coupled to the process communication module. The controller is configured to execute a number of improved diagnostic functions relative to the field device. The controller may obtain contextual information relative to a current field maintenance operation and preload at least one resource relative to a next field operation step. The controller may obtain process alarm information through a wireless communication module and field device alert information through the process communication module and provide an indication on a display relative to both process alarm information and field device alert information. The controller may execute a sequence of field device maintenance operations on the field device in response to a signal from a user input device. The controller may obtain snapshot information in response to a signal from a user input device.

DETAILED DESCRIPTION

Figure 1A:
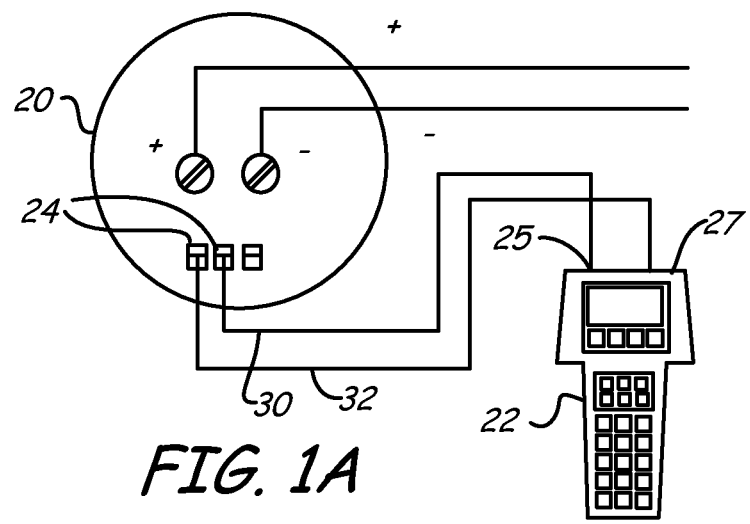
FIGS. 1A and 1B are diagrammatic views of a handheld field maintenance tool with which embodiments of the invention are particularly useful.
Figure 1B:
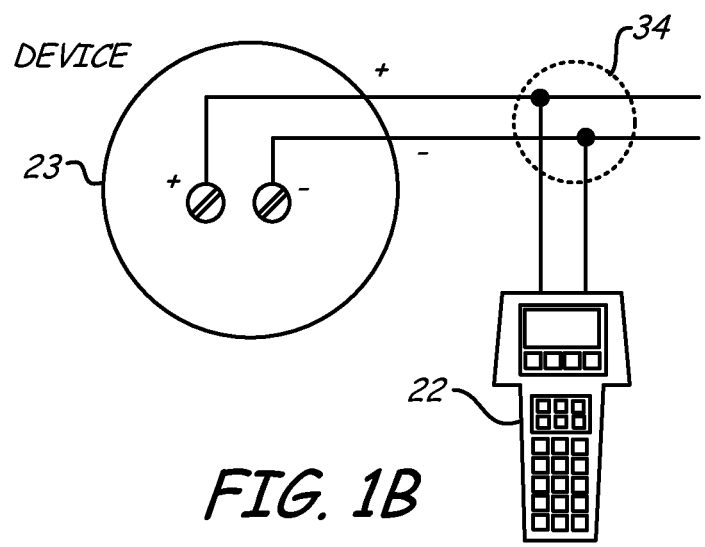

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23.

Figure 2:
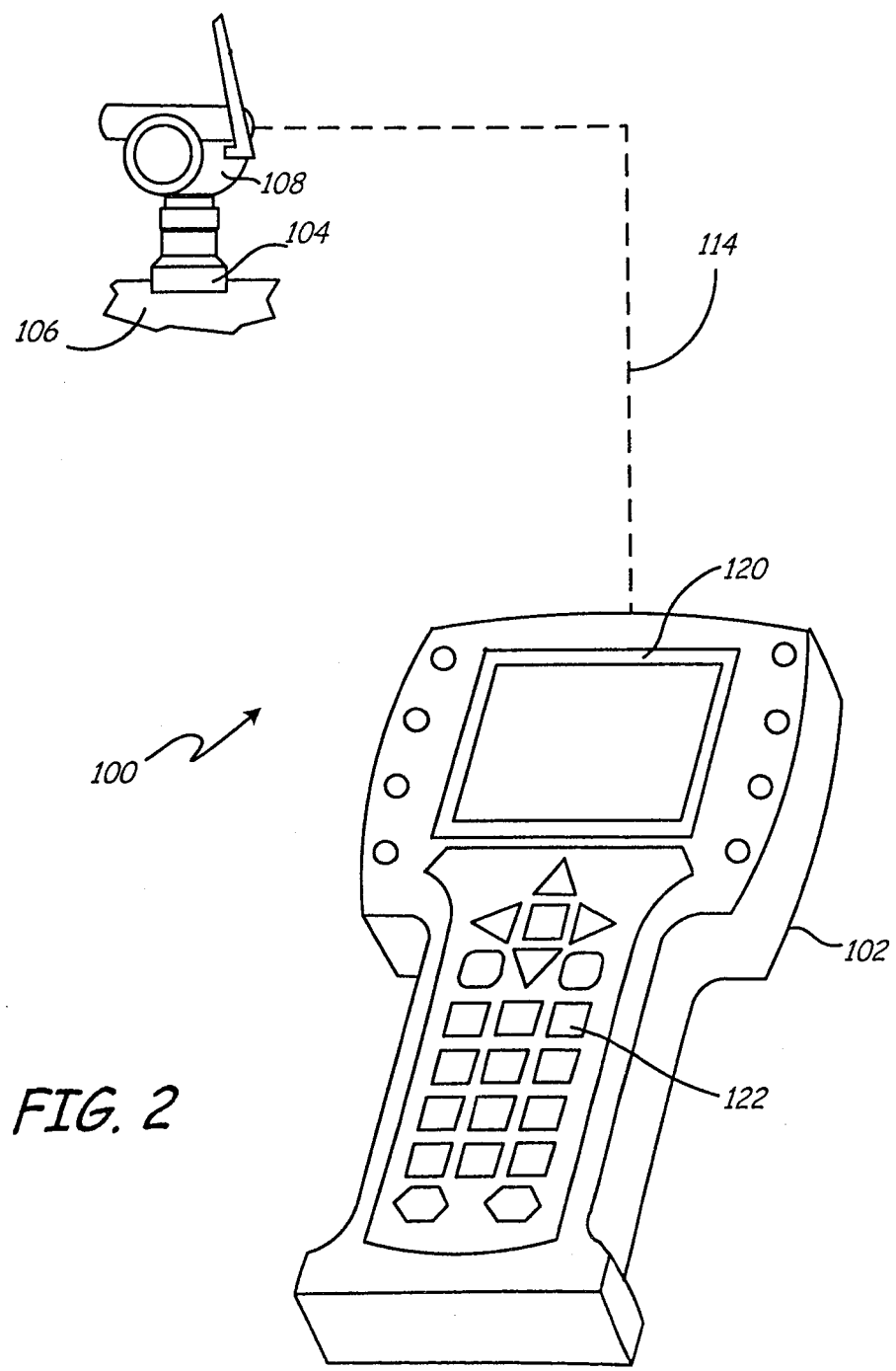
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus and/or the HART® protocol. Handheld field maintenance tools, such as tool 102 can be used to save configuration data from field devices, such as field device 104.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of user input buttons 122. Display 120 may be any suitable display such as an active-matrix liquid crystal display, or any other suitable display that is able to provide useful information. Buttons 122 may comprise any suitable arrangement of buttons relative to any number of functions to which the handheld field maintenance tool may be directed. Buttons 122 may comprise a numeric keypad, an alphanumeric keypad, any suitable number of custom functions and/or navigation buttons, or any combination thereof.

Figure 3:
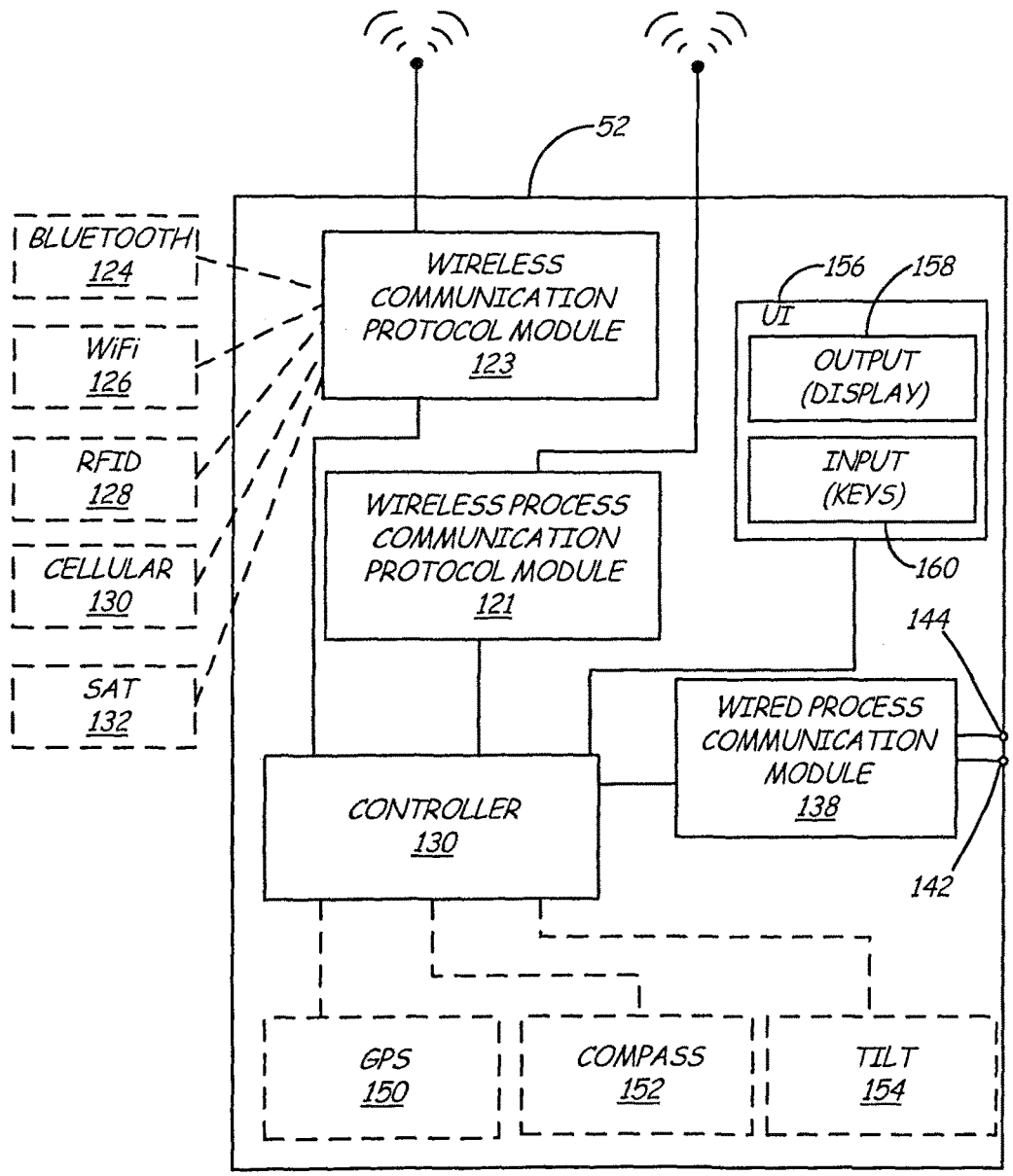
FIG. 3 is a block diagram of a handheld field maintenance tool in accordance with an embodiment of the present invention.

FIG. 3 is a diagrammatic system block diagram of a handheld field maintenance tool in accordance with the embodiment of the present invention. It is preferred that tool 52 comply with at least one intrinsic safety specification, such as that listed above, in order to help ensure safety in potentially explosive environments. Handheld field maintenance tool 52 preferably includes at least one wireless process communication module 121. Suitable examples for wireless process communication module 121 include a module that generates and/or receives proper signals in accordance with a known wireless communication protocol, such as the known WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2); a Wi-Fi specification 126 (such as IEEE 802.11.a/b/g/n); a known RFID specification 128; cellular communication techniques 130 (such as GSM/CDMA); WiMAX (IEEE 802.16m), and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138.

Embodiments of the present invention generally leverage the wireless communication abilities of the handheld field maintenance tool to create a persistent, real-time data communication pathway or channel with the process installation network or cloud. Such access can be done using a direct wireless connection to the process installation network, or through a Virtual Private Network (VPN) tunnel into the process installation network through a process installation network firewall. This provides the ability for the handheld field maintenance tool to automatically interact and/or synchronize with systems within the process installation data network, such as an asset management system, a Computerized Maintenance Management System (CMMS), a Distributed Control System (DCS), et cetera. In some process installations, wireless communication may not be possible due to interference or the lack of a wireless access point within range of the handheld field maintenance tool. In such situations, the controller of the handheld field maintenance tool is preferably configured to store various data to be synchronized, such that when a suitable "hot spot" is found where wireless connectivity is available, the handheld field maintenance tool can connect and synchronize with suitable servers or other remote devices.

Controller 130 is preferably a microprocessor that executes a sequence of instructions stored therein, or in memory coupled to controller 130, to perform handheld field maintenance tasks. Wired process communication module 138 allows handheld field maintenance tool 52 to be physically coupled via a wired connection at terminals 142, 144 to a field device. Examples of suitable wired process communication include the highway addressable remote transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further still, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121. Such triangulation techniques can also be employed if a suitable number of wireless interactions with fixed-position wireless field devices can be achieved. Finally, while the various methods provided for obtaining the position of handheld field maintenance tool 52 are described above, they can also be used in conjunction with one another to provide additional accuracy and/or redundancy. Additionally, tool 52 also preferably comprises compass module 152 coupled to controller 130 such that tool 52 can indicate the compass direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

When one or more field devices are not functioning properly the entire process installation may be affected. It is thus very important for problems with such devices to be identified and remedied as quickly as possible. Moreover, with modern smart field devices growing more complex, finding a root cause of a specific problem is becoming more difficult.

In accordance with an embodiment of the present invention, a handheld field maintenance tool provides advanced diagnostic and troubleshooting functions for a field technician. Additionally, such advanced functionality is preferably provided using simplified user interface techniques such that the overall diagnostic task for the field technician is simplified while the actual diagnostics performed using the handheld field maintenance tool become more complex or advanced.

One manner in which field maintenance is simplified is by providing a handheld field maintenance tool that supports work flows. Field maintenance tasks are preferably grouped with applications and other information in a logical arrangement that is consistent with work flows used by technicians in the field. When in "workflow" mode, the handheld field maintenance tool senses, measures, or otherwise obtains, information about what the technician is currently doing, the next step(s) that the technician will likely take. With such information, the handheld field maintenance tool can make relevant information and applications readily accessible to the technician. Examples of such context information that can inform the handheld field maintenance tool about what the technician is currently doing includes, but is not limited to, digital interactions with a connected field device; errors or other diagnostic information provided by the field device; field device status information; field device audit trail information (preferably obtained wirelessly from an asset management system in real-time); asset history information (either stored locally in the handheld field maintenance tool or obtained wirelessly from a remote host); process parameters relative to the process installation, which are provided by one or more other field devices or the process controller; field device alert information (available from the connected field device or another field device); process alarm conditions; local environmental conditions (such as ambient temperature, barometric pressure, humidity, et cetera); measurement of electromagnetic interference using any of the wireless communication modules within the handheld field maintenance tool; vibration measurement; time of day; information relative to the technician (such as technician name or ID, technician security clearance, et cetera). Any such parameters, either alone or in combination with other parameters, can inform the handheld field maintenance tool about what the technician is currently doing. While the result of analyzing such information preferably indicates a specific tack for which next steps, information and/or application can be provided, it is expressly contemplated that a number of viable results can be determined with a statistical weight ranking the results. Thus, next step information, applications, et cetera can be provided for not only the top result, but even the top plurality of results. Moreover, while such diverse information is preferably automatically analyzed by the handheld field maintenance tool in order to assist the technician with the next logical step(s) in his or her field maintenance, it is also contemplated that all such information can also be made available to the technician.

Figure 4:
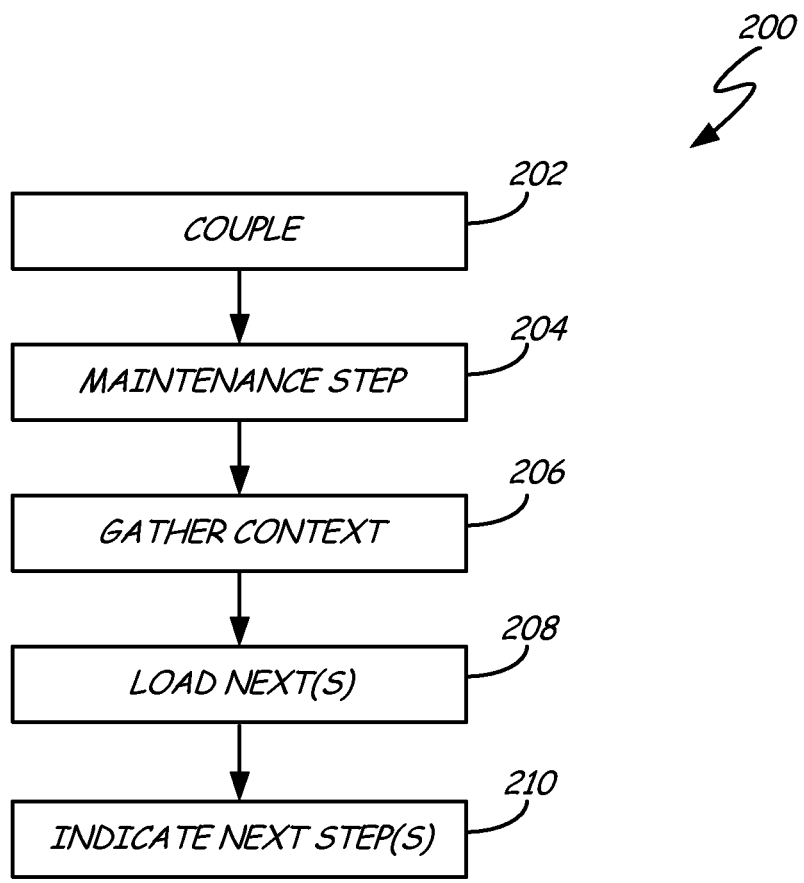
FIG. 4 is a diagrammatic view of a method of facilitating field maintenance with a handheld field maintenance tool in accordance with an embodiment of the present invention.

FIG. 4 is a diagrammatic view of a method of facilitating field maintenance with a handheld field maintenance tool in accordance with an embodiment of the present invention. Method 200 begins at block 202 where a handheld field maintenance tool is communicatively coupled to a field device. Such communicative coupling may be a wired coupling (either directly to the field device or through a process communication loop or segment) or a wireless coupling. Next, at block 204, the handheld field maintenance tool is used to execute at least one field maintenance function relative to the field device. At block 206, the handheld field maintenance tool acquires context information regarding the current field maintenance activity. This step is preferably done automatically without technician input. Based on the information obtained at step 206, controller 130 in handheld field maintenance tool 52 determines what activity the technician is currently performing. Based on the current technician activity, controller 130 determines one or more next steps, and determines resources needed for the one or more next steps. The resources are loaded at block 208, such that when the technician completes the current activity, the resource(s) required for the probable next step is/are already available. At block 210, the most likely next step is indicated to the user through display 120. The technician may select the indicated step, or may indicate that the proposed next step is not accepted. In such case, method 200 may provide the next most likely next step to the technician, or may simply allow the technician to end the context-sensitive resource pre-loading.

Embodiments of the present invention can also be used to facilitate documentation of the maintenance steps performed by the technician. For example, upon completion of each step performed, the results of that step may be stored in the handheld field maintenance tool, an asset management system, a CMMS system, et cetera to maintain a historical record of the work performed on a particular field device. Such information may include a description of the work done, whether the work was successful or not, a pass/fail rating, notes, et cetera. The handheld field maintenance tool preferably automates the acquisition of such information, but embodiments of the present invention also include receiving manual data entry from the technician on the handheld field maintenance tool relative to any of the information listed above. The results for individual maintenance steps are preferably aggregated to produce summary information about the whole procedure. This summary rating/information could include a check mark, or other suitable flag, for completion, a pass/fail rating, data, notes et cetera. The results are preferably stored on the handheld field maintenance tool and uploaded to an asset management system or higher level information system, et cetera for analysis and/or archival. The results could then be used by a maintenance manager to ensure that work had been completed as expected.

While embodiments of the present invention generally obtain and process significant amounts of diagnostic and/or contextual information, it is prefer that at least some embodiments of the present invention provide the technician with a simplified display that combines such data. This simplified indication may be provided on display 120 automatically, or may be selected or otherwise invoked by the technician. For example, one such simplified diagnostic indication is a simple good/bad indicator that provides a general indication of the health of the field device. It may be as simple as a good/bad flag or icon, or it may indicate a continuum between good and bad. Additionally, device-specific help information is also provided to the technician as desired. For example, the technician may select the "help" function or key, and the handheld field maintenance tool automatically generates a query to a remote host or system relative to the specific field device to which the handheld field maintenance tool is communicatively coupled. The query results are received wirelessly and displayed to the technician. Preferably, the help results are analyzed based on current field device context information, and more particular items of help information are offered to the technician based on the context information. Help results can include any information that is helpful to the technician drawn from any source, local or remote. Examples of help results include help information from a field device manual, a list of tasks (with links to the DD tasks) to perform based on the status, as well as one or more resources to "fix" the field device. Help results can also include links to videos where the technician is shown how to diagnose/troubleshoot/fix the field device. In embodiments where the handheld field maintenance tool has sufficient memory capacity, all device-specific help information may actually be stored locally. However, in such embodiments, it is still preferred that the help query results be ordered or organized based on the context information. Thus, if a technician is performing a specific calibration operation on a specific field device and presses the help button, the result will be device-specific help information, and the highest ranking result will be directed to the calibration operation the technician is currently performing.

One difficulty that faces technicians when they investigate, troubleshoot and diagnose problems in a running process is not having visibility to the field device alert and process alarm conditions simultaneously. In order to diagnose problems, the technician must generally be in constant contact with another worker inside the control room who is looking at the alarm banner on the operator screen.

Figure 5:
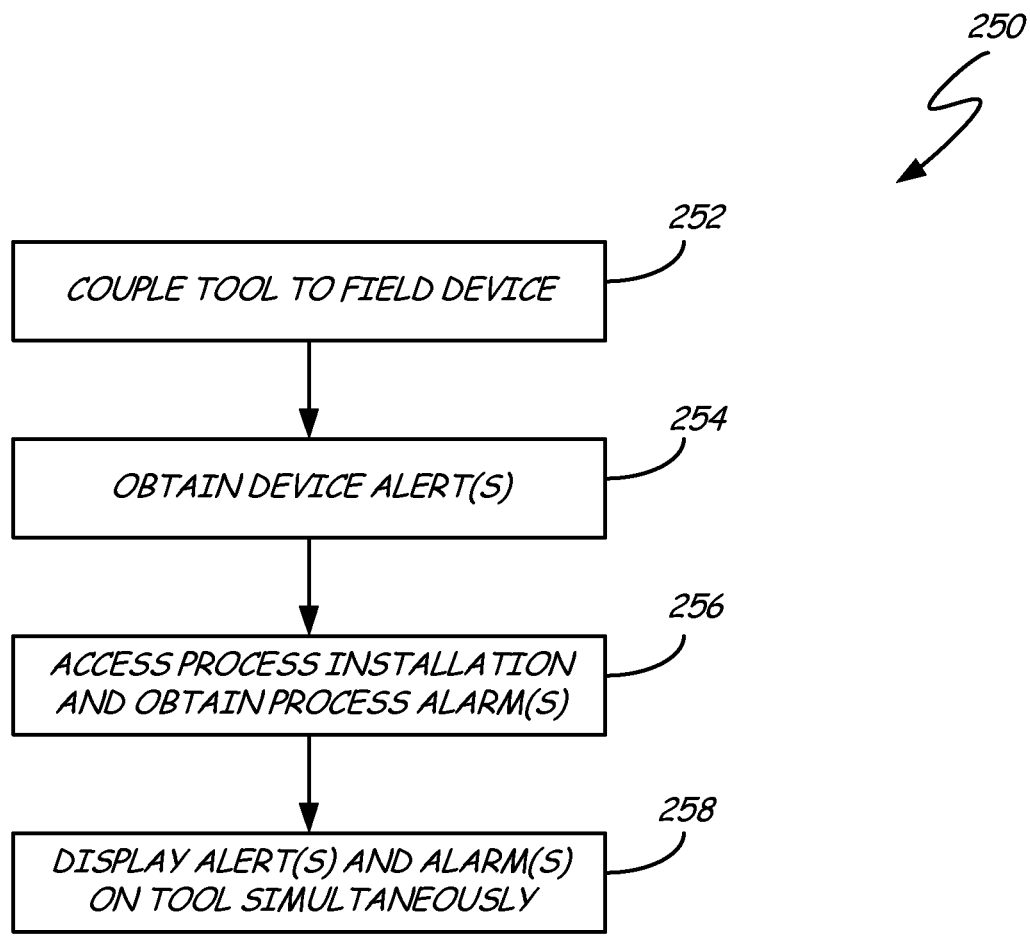
FIG. 5 is a block diagram of a method of providing device alert and process alarm conditions on a handheld field maintenance tool in accordance with an embodiment of the present invention.

FIG. 5 is a block diagram of a method of providing device alert and process alarm conditions on a handheld field maintenance tool in accordance with an embodiment of the present invention. Method 250 begins at block 252 where the handheld field maintenance tool is communicatively coupled to the field device. Preferably, whenever the handheld field maintenance tool is communicatively coupled to a field device, the tool will automatically identify the field device and load, or otherwise obtain a device description for the connected field device. At block 254, the field device is interrogated and one or more device alerts are obtained from the field device. Such alerts may indicate the occurrence of a specified event or condition that has occurred or is currently occurring. At block 256, the handheld field maintenance tool communicates with a control room host or system that is currently running the process. Such communication is preferably wireless communication. The control room host or system provides information to the handheld field maintenance tool relative to one or more process alarms. A process alarm is an indication that a specified alarm condition has been satisfied and is not yet resolved. A process alarm can be related to a number of process conditions. For example, a process alarm can be related to a process variable, such as a process pressure, a field device failure or deterioration, process communication difficulties, et cetera. At block 258, the handheld field maintenance tool generates an indication on display 120 that shows both device alerts and process alarms simultaneously. This provides the technician, in the field, with a display of process alarm conditions that the process operator sees, along with a summary of detected field device alerts. Using both displays, the technician in the field can quickly pinpoint the source of the problem and arrive at a diagnosis for resolution. While the description above is provided relative to process alarms and device alerts, any relevant process information from the process control system can be provided. Examples include process variables, analog output values, setpoints, et cetera.

Figure 6:
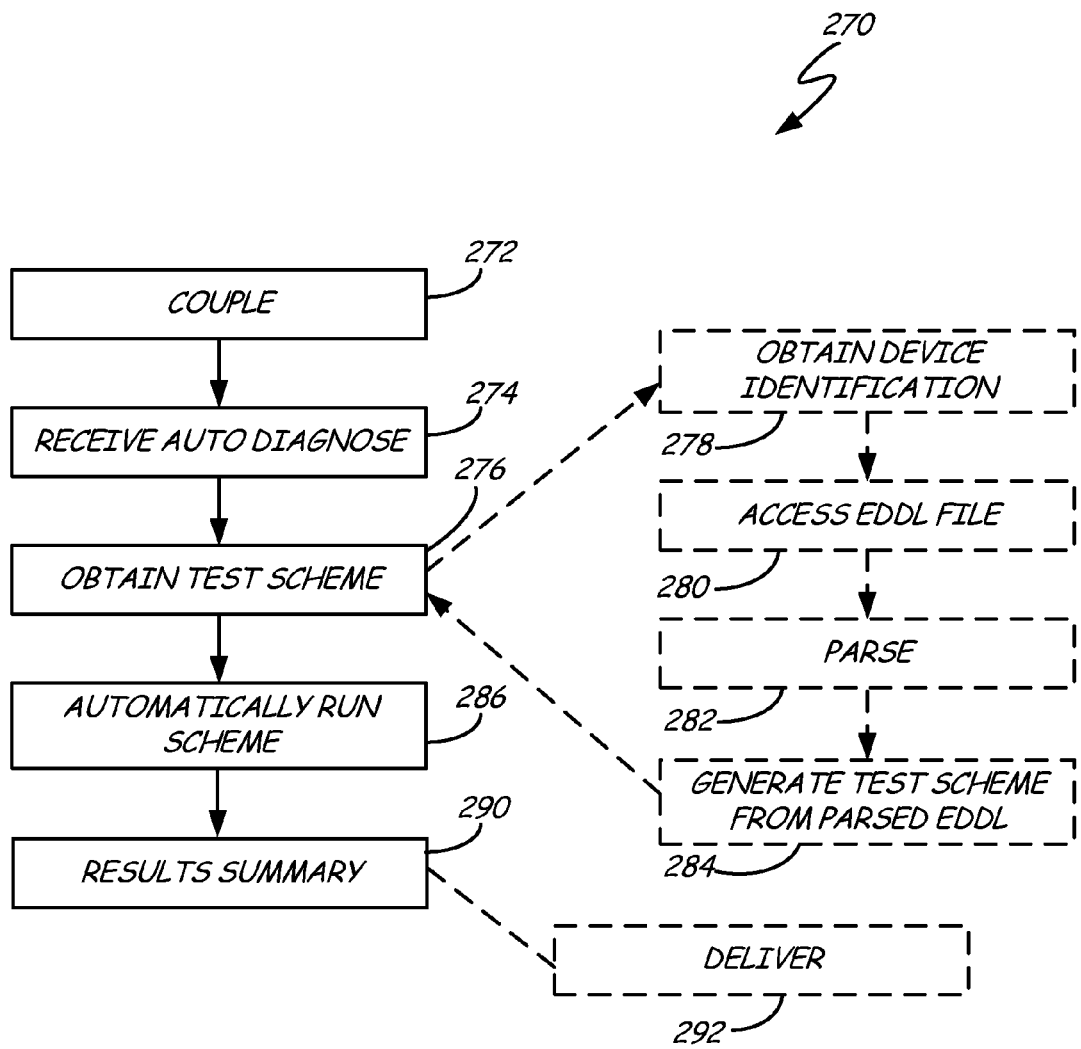
FIG. 6 is a flow diagram of a method of simply executing complex, device-specific diagnostics using a handheld field maintenance tool in accordance with an embodiment of the present invention.

FIG. 6 is a flow diagram of a method of simply executing complex, device-specific diagnostics using a handheld field maintenance tool in accordance with an embodiment of the present invention. Method 270 begins at block 272 where a handheld field maintenance tool is communicatively coupled to a field device. At block 274, the handheld field maintenance tool receives a technician input that selects the automatic diagnostic function. This selection may be generated in any suitable manner, however, it is preferred that the automatic diagnostic function be selectable with a single keypress. For example, a function-specific physical button may be included among buttons 122. Additionally, once the handheld field maintenance tool is communicatively coupled to a field device, a soft-key may be available that allows the automatic diagnostic function to be invoked with the single keypress. The soft-key may be a physical button 122 in proximity to display 120, such that display 120 may indicate a label proximate the soft-key that is indicative of the soft-key function.

At block 276, the handheld field maintenance tool obtains a test scheme for the specific field device to which it was communicatively coupled in block 272. Obtaining the test scheme can be done in any suitable manner, but is preferably done as indicated by the blocks in phantom. Specifically, the handheld field maintenance tool first identifies the field device to which it is coupled. This identification may include obtaining device tag information or some other identifier. The field device may also provide an indication of model number, manufacturer, device revision number, and device description revision number. In instances where the field device is not able to provide such information, the handheld field maintenance tool can preferably use its wireless communication to interact with an asset management system to obtain such information based on a lookup of the device tag. In any event, at block 280, the handheld field maintenance tool accesses an electronic device description (EDD) file that corresponds with the exact field device manufacturer, model number and revision number that was obtained at block 278. Such access may be performed using wireless communication, and/or may be performed using a local database lookup (in embodiments where the handheld field maintenance tool stores one or more EDD files). An electronic device descriptor (EDD) is written using electronic device description language (EDDL) and includes an exhaustive list of all tests that the specific field device needs to pass in order to be considered free of errors and defects. Field devices include or are provided with this information, but it is not easily usable by a technician. Thus, at block 282, the handheld field maintenance tool causes controller to parse, or otherwise process, the EDD file to generate one or more automated test scripts that comprise a test scheme, as indicated at block 284. While the description provided above specifically references EDD files, any computer-readable media that provides a description of an associated field device can be used in accordance with embodiments of the present invention. Suitable examples include Field Device Tool/Device Type Manager (FDT/DTM) in accordance with the FDT Specification managed by FDT Group AISBL, Field Device Integration (FDI), et cetera.

At block 286, the handheld field maintenance tool begins automatically executing the test scheme. Preferably, the test scheme is executed without any technician intervention. However, it is contemplated that if certain tests or scripts require physical acts (such as connecting a reference resistance to a pair of field device sensor terminals). Even with technician intervention, the sequence of individual test scripts as well as communication with the field device is still preferably performed automatically. Once all test scripts in the scheme have run, the handheld field maintenance tool preferably provides a summary of the results to the technician, as indicated at block 290. The summary preferably lists each test script, and a result of each script. Results can include an indication of whether the field device passed the test, failed the test, or whether the result was indeterminate. Moreover, the results summary can also include alert conditions and/or problems discovered. Preferably, the automatic diagnostic will also include as-found data that was recorded prior to running the test scheme. Additionally, if the field device does have problems or failures the final summary or report can provide one-click access to device-specific help relative to the specific problem(s) encountered and/or steps for the technician to correct or further investigate the problem. Moreover, the handheld field maintenance tool may also access a repair manual relative to the specific problem, such that the manual can be consulted directly on the handheld field maintenance tool. Field device manuals are typically available online in a standard format such as the known .pdf format. At block 292, the results can also be delivered as required. Delivery can include printing a hardcopy (for example, printing via a Bluetooth printer), or emailing the results to an address specified by the technician.

Embodiments described above generally help the technician to perform a number of tasks or operations to ascertain a cause of a problem in a field device. However, sometimes, after all tests have been run, and information has been studied, the problem is still not identified. In such instances, embodiments of the present invention also facilitate interaction with a third-party support entity, such as the customer-support group of the field device's manufacturer.

Figure 7:
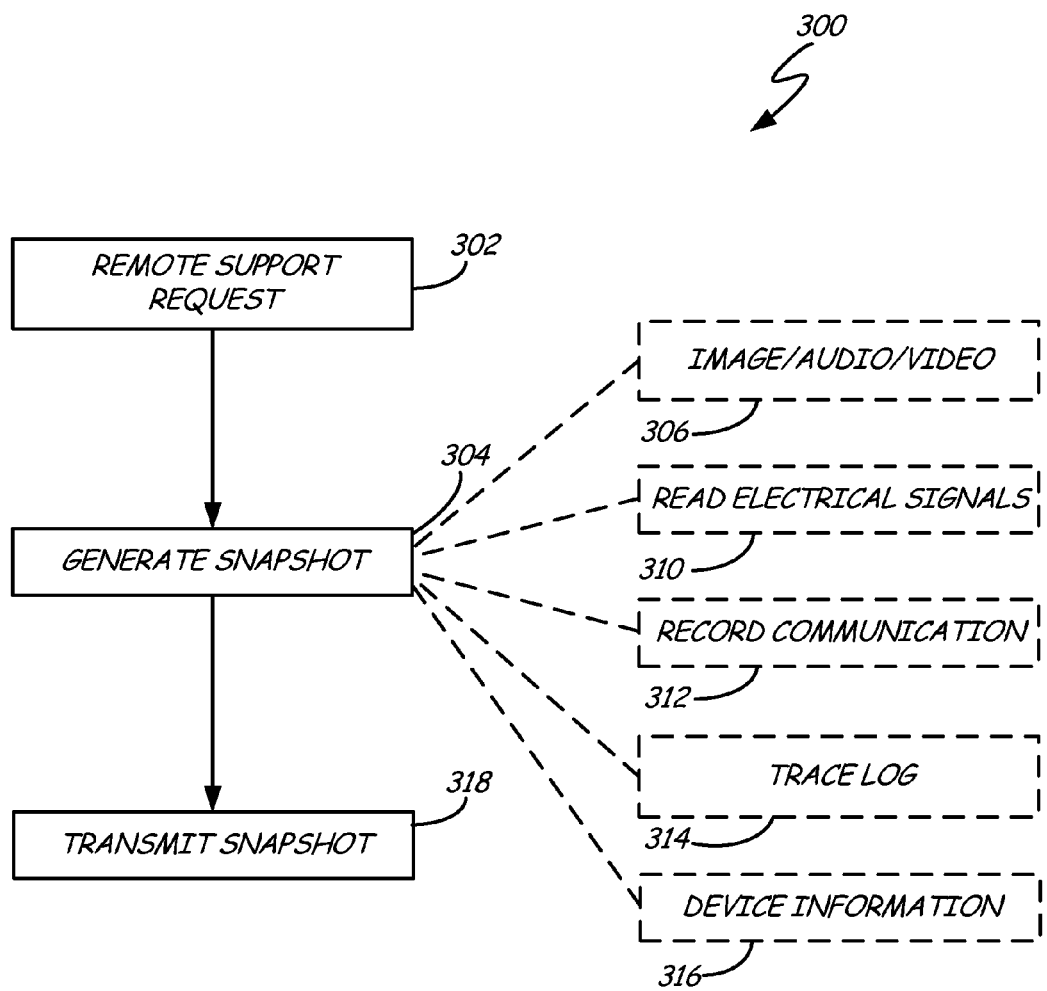
FIG. 7 is a flow diagram of a method of providing diagnostic information to a remote party using a handheld field maintenance tool in accordance with an embodiment of the present invention.

FIG. 7 is a flow diagram of a method of providing diagnostic information to a remote entity using a handheld field maintenance tool in accordance with an embodiment of the present invention. Method 300 beings at block 302 wherein a technician provides an input indicating a request for remote support. The user input may also be indicative of one particular remote support provider among a plurality of providers. For example, one provider may be an expert group located at the process installation, while another provider may be the manufacturer's customer support group. For each such provider, the handheld field maintenance tool preferably includes, or otherwise obtains, a pointer or indicator. One example of such an indicator is an email address. However, the pointer or indicator may also be a uniform resource locator (URL) of a secure ftp server that is configured to receive diagnostic information from handheld field maintenance tools. Moreover, embodiments of the present invention also contemplate the ability of the technician to select a plurality of providers.

At block 304, the handheld field maintenance tool gathers snapshot information. As used herein, snapshot information includes any information relative to the field device, interaction with the field device, and/or contextual information. Snapshot information may include an actual photograph, video, and/or audio of the field device operating, or otherwise, in the field, as indicated at block 306. Snapshot information may also include specific electrical measurements obtained or otherwise determined relative to the field device, as indicated at block 310. The snapshot information may also include a copy of any or all communication between the handheld field maintenance tool and the field device, as indicated at block 312. Snapshot information may also include a trace log to track the steps that were taken by the technician, as indicated at block 314. Snapshot information may further include any suitable device information, such as device tag, model number, revision number, serial number, lot code, et cetera. Further still, snapshot information may include any of the context information listed above with respect to the embodiment that pre-loads resources based on what the technician is currently doing. While the description of method 300 provides a description of block 302 before block 304, the order can, in fact, be reversed. Thus, a technician may gather snapshot information before requesting remote support. The acquisition of the snapshot information may happen automatically, where the system simply gathers the data in anticipation of the remote support request, or it could be technician-invoked.

At block 318, the snapshot information is transmitted to the remote support provider. In embodiments where the handheld field maintenance tool has real-time wireless communication, the transmission may be done while the handheld field maintenance tool is still communicatively coupled to the field device. Additionally, or alternatively, the transmission may be stored until the handheld field maintenance tool has a wireless, or wired connection. Additionally, the snapshot information may also be transmitted to an asset management system for archival relative to the field device.

Figure 8:
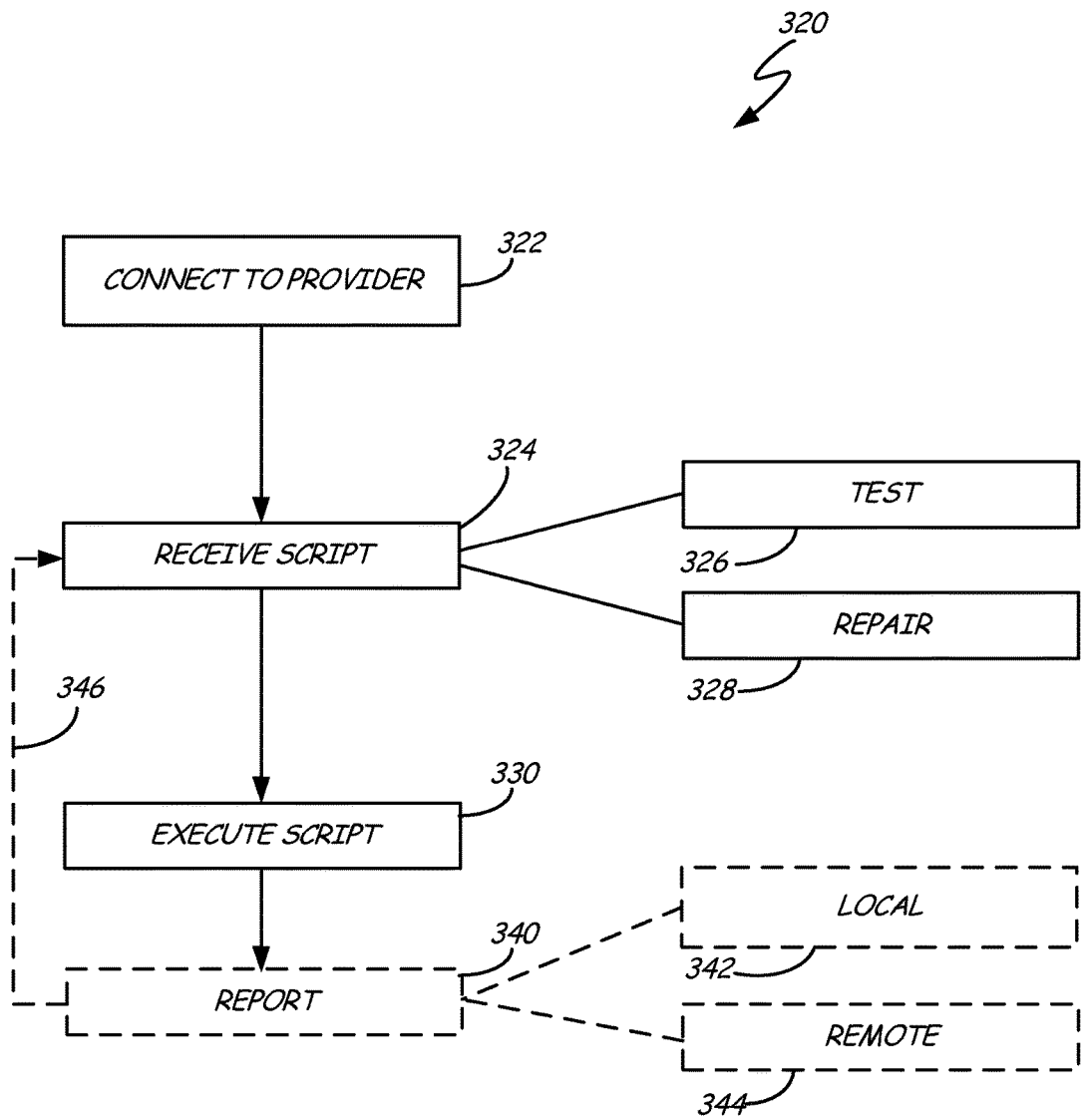
FIG. 8 is a flow diagram of a method of receiving remote support using a handheld field maintenance tool in accordance with an embodiment of the present invention.

FIG. 8 is a flow diagram of a method of receiving remote support using a handheld field maintenance tool in accordance with an embodiment of the present invention. Method 320 preferably executes after method 300 described above. However, this may not always be necessary. While it is probable, that snapshot information is very informative for the method of providing remote support, embodiments of the present invention can be practiced where a technician simply selects remote support relative to a specific field device and receives one or more test scripts or resources from the remote support provider. At block 322, the handheld field maintenance tool establishes a communication connection with the selected remote support provider. At block 324, the handheld field maintenance tool receives a test script 326 and/or a repair script 328. As set forth above, the scripts received from the remote support provider are preferably in response, or after, the submission of a snapshot to the remote support provider as described with respect to FIG. 7. Next, at block 330, the handheld field maintenance tool automatically executes one or more test/repairs scripts received from the remote support provider on the field device. At block 340, the handheld field maintenance tool determines the results of the remote script execution. These results may be provided locally 342 on the display 120 of the handheld field maintenance tool, and/or remotely 344 to the remote support provider. Upon providing the results to the remote support provider, one or more additional test or repair scripts may be received thus returning control to block 324 via line 346.

Although the present invention has been described with reference to particular embodiments, workers skilled in the art will recognize that changes may be made in form and detail without departing from the spirit and scope of the invention.

What is claimed is:

1. A handheld field maintenance tool comprising:
   a wired process communication module configured to interact with a field device, wherein the wired process communication module is configured to be physically coupled to the field device to interact with the field device;
   a wireless communication protocol module configured to communicatively couple the handheld field maintenance tool to a remote source;
   a controller coupled to the wired process communication module and the wireless communication protocol module, the controller being configured to support a workflow mode, in which the controller is configured to:
      automatically obtain contextual information relative to an unknown current step in a field maintenance operation;
      identify the unknown current step being executed in the field maintenance operation based on the contextual information obtained;
      identify a subsequent step of the field maintenance operation, in a workflow currently being executed, based on the identification of the unknown current step;
      pre-load at least one resource based on the identified subsequent step; and
      present the user with subsequent step information through a display, wherein the subsequent step information is displayed after the identified current step is completed and comprises the at least one resource and the subsequent step of the field maintenance operation.

2. The handheld field maintenance tool of claim 1, wherein the handheld field maintenance tool complies with an intrinsic safety specification.

3. The handheld field maintenance tool of claim 1, wherein at least some contextual information is obtained from a remote device through the wireless communication protocol module.

4. The handheld field maintenance tool of claim 1, wherein the wired process communication module interacts with the field device using a HART protocol.

5. The handheld field maintenance tool of claim 1, wherein the wired process communication module interacts with the field device using a FOUNDATION Fieldbus protocol.

6. A handheld field maintenance tool comprising:
   a wired process communication module configured to interact with a field device, wherein the wired process communication module is configured to be physically coupled to the field device to interact with the field device;
   a wireless communication protocol module configured to communicatively couple the handheld field maintenance tool to a remote source;
   a controller coupled to the wired process communication module and the wireless communication protocol module, the controller being configured to, upon entering a workflow mode of operation:
      automatically obtain contextual information relative to an unknown current step in a field maintenance operation from the field device, using the wired process communication module;
      identify the unknown current step of the field maintenance operation based on the contextual information obtained from the field device;
      identify a plurality of optional next steps based on the identification of the unknown current step in the field maintenance operation;
      organize the plurality of optional next steps based on a statistical weight ranking, wherein the plurality of optional next steps is organized based on a probability of occurrence after the identified current step of the field maintenance operation is completed;
      determine at least one resource related to a most likely next step of the organized plurality of optional next steps, wherein the at least one resource is configured to assist a technician with the most likely next step;
      obtain the at least one resource from the remote source using the wireless communication protocol module prior to the completion of the identified current step of the field maintenance operation; and
      present the organized plurality of optional next steps, the most likely next step and the at least one resource on a display after completion of the identified current step of the field maintenance operation.

7. The handheld field maintenance tool of claim 6, wherein the handheld field maintenance tool is further configured to store a set of results corresponding to the completed current step of the field maintenance operation.

8. The handheld field maintenance tool of claim 6, wherein the controller is further configured to generate an operation summary.

9. The handheld field maintenance tool of clam 6, wherein the handheld field maintenance tool complies with an intrinsic safety specification.

10. A method of facilitating a field maintenance operation using a handheld field maintenance tool, the method comprising:
   receiving a user input on the handheld field maintenance tool, wherein the user input indicates that the handheld field maintenance tool enter a workflow mode of operation, and upon entering the workflow mode of operation, performing the steps of:
      automatically obtaining contextual information from a field device, using a wired process communication module of the handheld field maintenance tool, wherein the contextual information comprises at least information regarding an unknown current step of the field maintenance operation;
      identifying the unknown current step of the field maintenance operation, using a controller of the handheld field maintenance tool, based on the contextual information received;
      identifying, based on the identified current step of the field maintenance operation, a likely next step of the field maintenance operation;
      obtaining a resource associated with the likely next step of the field maintenance operation from a remote source, using a wireless communication protocol module of the handheld field maintenance tool;

presenting the likely next step and the resource on a display of the handheld field maintenance tool after completion of the identified current step of the field maintenance operation; and storing a set of results based on the completion of the identified current step.

11. The method of facilitating a field maintenance operation of claim 10, further comprising:

receiving an additional user input indicating that the likely next step and the resource are not relevant; and presenting an alternative likely next step on the display of the handheld field maintenance tool.

12. The method of facilitating a field maintenance operation of claim 10, further comprising:

generating a summary after the field maintenance operation is completed, using the controller of the handheld field maintenance tool; and storing the summary in a memory of the handheld field maintenance tool.

13. The method of facilitating a field maintenance operation of claim 12, wherein the summary comprises an indication of whether the operation was completed.

14. The method of facilitating a field maintenance operation of claim 12, wherein the summary comprises an indication of whether the field maintenance operation was successful.

15. The method of facilitating afield maintenance operation of claim 12, further comprising:

sending the summary to an asset management system after the summary is stored, using the wireless communication protocol module of the handheld field maintenance tool.

16. A method of facilitating a diagnostic task using a handheld field maintenance tool, the method comprising:

receiving a user input on the handheld field maintenance tool, wherein the user input indicates that the handheld field maintenance tool enter a workflow mode of operation, and upon entering the workflow mode of operation, performing the steps of;

automatically obtaining contextual information from a remote source, using a wireless communication module of the handheld field maintenance tool, wherein the contextual information comprises at least information regarding an unknown current step of the diagnostic task;

identifying the unknown current step of the diagnostic task based on the contextual information received;

identifying, based on the identified current step of the diagnostic task, a likely next step of the diagnostic task and an alternative likely next step;

obtaining a resource associated with the likely next step of the diagnostic task from the remote source, using the wireless communication protocol module of the handheld field maintenance tool;

presenting the likely next step and the resource on a display of the handheld field maintenance tool after completion of the identified current step of the diagnostic task;

receiving an additional user input indicating that the likely next step and the resource are not relevant; and presenting the alternative likely next step on the display of the handheld field maintenance tool.

17. The method of facilitating a field maintenance operation of claim 16, further comprising:

storing a set of results, in the handheld field maintenance tool, based on the completion of the identified current step of the diagnostic task.

18. The method of facilitating a field maintenance operation of claim 17, wherein the set of results includes a description of the completed, identified current step of the diagnostic task.

19. The method of facilitating a field maintenance operation of claim 17, wherein the set of results includes an indication of whether the identified current step was successfully completed.

20. The method of facilitating a field maintenance operation of claim 18, wherein the set of results are stored in a memory of the handheld field maintenance tool.

21. The handheld field maintenance tool of claim 1, wherein the contextual information comprises at least information relative to the field device and a record of communication between the handheld field maintenance tool and the field device.

22. The handheld field maintenance tool of claim 1, further comprising a position detection module.

23. The handheld field maintenance tool of claim 22, wherein automatically obtaining contextual information includes determining a position of the handheld field maintenance tool using the position detection module.

24. The handheld field maintenance tool of claim 23, further comprising a tilt module.

* * * * *

UNITED STATES PATENT AND TRADEMARK OFFICE
CERTIFICATE OF CORRECTION

PATENT NO. : 9,709,973 B2  
APPLICATION NO. : 13/191644  
DATED : July 18, 2017  
INVENTOR(S) : Todd M. Toepke et al.

Page 1 of 1

It is certified that error appears in the above-identified patent and that said Letters Patent is hereby corrected as shown below:

In the Claims

Column 13  
Claim 15:  
Line 29:  
Change "afield" to "a field"

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*